United States Patent [19]

Ecke, Jr.

[11] Plant 4,810

[45] Jan. 19, 1982

[54] POINSETTIA NAMED V-10 MARBLE

[75] Inventor: Paul Ecke, Jr., Encinitas, Calif.

[73] Assignee: Paul Ecke Ranch, Encinitas, Calif.

[21] Appl. No.: 185,125

[22] Filed: Sep. 5, 1980

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Rummler and Snow

[57] ABSTRACT

A new and distinctive variety of poinsettia plant distinguished by the distinctive coloration of its bracts, which are marbled with shades of white and pink, and further characterized by being substantially identical with the red GUTBIER'S V-10 (U.S. Plant Pat. No. 4,235) except with respect to color of the bracts.

1 Drawing Figure

BACKGROUND OF THE NEW PLANT

This new poinsettia cultivar originated as a mutation of its parent GUTBIER'S V-10 PINK (application Ser. No. 185,123), which, in turn, was a mutation of the red variety GUTBIER'S V-10 (U.S. Plant Pat. No. 4,235). This particular marbled selection was the result of many trials and tests carried on by me at Encinitas, Calif., with the object of obtaining good commercially-acceptable poinsettia varieties descended from and retaining all of the important advantages of the GUTBIER'S V-10 red variety. Upon my selection of this unique marbled mutation from among poinsettia plants growing in my greenhouse at Encinitas, Calif., I subjected the new variety to successive generations of propagation, by means of cuttings, and found that the new plant retained all of its distinctive and novel characteristics from generation to generation and which now appear to be firmly fixed.

DESCRIPTION OF THE DRAWINGS

This new poinsettia cultivar is illustrated by the accompanying full color photographic drawings, the upper one of which shows a full face view of the mature blooms and the lower one of which shows a potted plant of this variety in full bloom.

DESCRIPTION OF THE NEW PLANT

The following is a detailed description of my new poinsettia cultivar, as observed at Encinitas, Calif., with color designations according to the R.H.S. Colour Chart published by The Royal Horticultural Society of London, England.

THE PLANT

Origin: Mutation.

Parentage: GUTBIER'S V-10 Pink (application Ser. No. 185,123).

Classification:

*Botanic.*—*Euphorbia pulcherrima.*

*Commercial.*—Greenhouse chrysanthemum.

Form: Shrub.

Height: Short.

Growth habit:

*As a single stem.*—Upright and vigorous with self branching side shoots. Usually will not require a growth regulator.

*As a branched plant.*—Upright with very many stems producing a bushy, full appearance.

Growth rate: Very fast with rooting occurring within 10 to 15 days under automatic mist and the plant blooming within 8 to 9 weeks at a night temperature of 14° to 16° C.

Foliage: Alternate, horizontal, with medium persistence and in normal abundance.

*Leaf size.*—Medium. About 3 to 6 inches long and 2½ to 4½ inches wide.

*Leaf shape.*—Ovate, with acuminate apex and substantially entire margin.

*Aspect.*—Upper side — smooth and medium glossy. Under side — dull with ordinary venation.

*Color.*—Upper side — near RHS 137A. Under side — near RHS 146A.

*Retention.*—The foliage lasts well when kept at a low room temperature, i.e. below 20° C., and with good light intensity.

Bracts: Usually about 12 to 16 in number, in overlapping arrangement with a tight center which provides a full effect. Mature and over-ripe blooms develop increasing numbers of bracts, often as many as 25 to 30, which cascade in two or three layers thereby increasing the fullness of the bloom. Many of the bracts have a distinctive arched appearance.

*Size.*—Various. Up to 6 inches long and 4 inches wide.

*Shape.*—Ovate, acuminate with substantially entire margins with some dentations. Small bracts are elliptic in shape.

*Color.*—Upper side — near RHS 36B (but slightly lighter and greyer) with near RHS 51C as the pink shades on a cream-white background of near RHS 160C. Under side — substantially of the same range of shades as the upper side. Prominent veining makes precise colors of pink difficult to assess.

*Ribs and veins.*—Light green color appearing on the under side of the bracts.

*Retention.*—Long lasting.

In general, this new poinsettia plant is substantially the same as its grandparent, GUTBIER'S V-10 (U.S. Plant Pat. No. 4,235), insofar as the important characteristics of size, form, growth and blooming habits are concerned, the new plant differing only by the marbled pink and white coloration of its bracts.

I claim:

1. The new and distinctive poinsettia cultivar, substantially as herein shown and described, characterized by the pink and white coloration of its tightly centered and overlapping bracts appearing on a plant otherwise substantially identical with the variety GUTBIER'S V-10 (U.S. Plant Pat. No. 4,235).

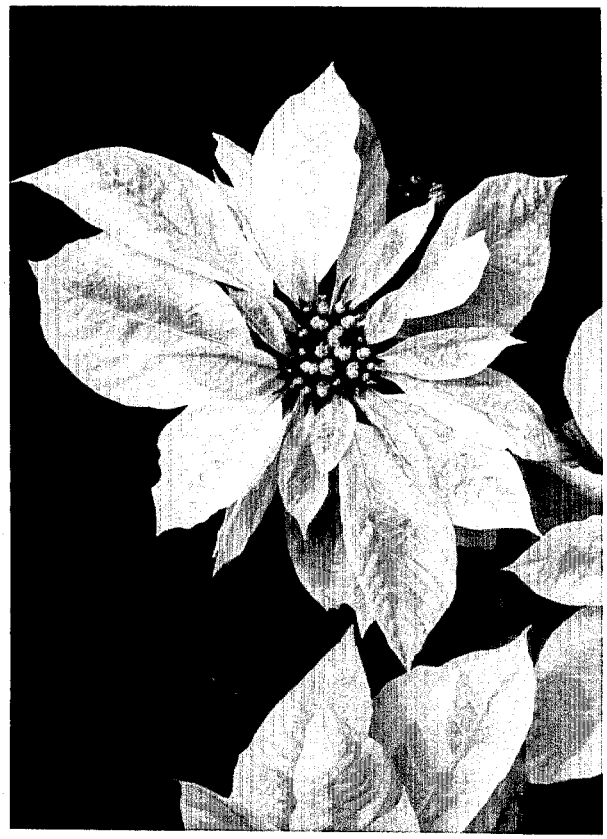
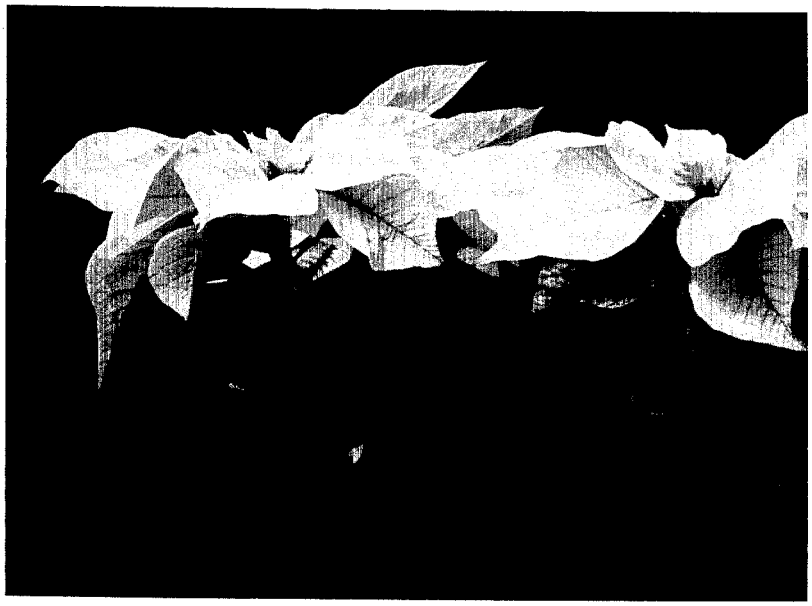

* * * * *